United States Patent [19]

Spector

[11] Patent Number: 4,819,656

[45] Date of Patent: Apr. 11, 1989

[54] BIOFEEDBACK THERAPY SYSTEM

[76] Inventor: Donald Spector, 380 Mountain Rd., Union City, N.J. 07087

[21] Appl. No.: 728,770

[22] Filed: Apr. 30, 1985

[51] Int. Cl.$^4$ .............................................. A61B 10/00
[52] U.S. Cl. ...................................... 128/736; 128/905
[58] Field of Search ............... 128/736, 905, 734, 732, 128/746, 741

[56] References Cited

U.S. PATENT DOCUMENTS

| | | | |
|---|---|---|---|
| 4,122,840 | 10/1978 | Tsuchiya et al. ................ | 128/905 X |
| 4,166,452 | 9/1979 | Generales, Jr. ...................... | 128/741 |
| 4,437,471 | 3/1984 | Nelson ................................. | 128/736 |

OTHER PUBLICATIONS

Mulke; "Bio-Control"; *Elektor;* Jul.-Aug. 1979, vol. 51/52, No. 7-8.

*Primary Examiner*—Kyle L. Howell
*Assistant Examiner*—Angela D. Sykes
*Attorney, Agent, or Firm*—Michael Ebert

[57] ABSTRACT

A biofeedback therapy system in which an individual during a training run in stress control is intermittently subjected to stress-inducing stimuli while one of his physiologic functions is being continuously monitored. The individual is able to observe the effect of the stimuli on a stress-graduated tripartite scale, making it possible for the individual to regulate the function being monitored. The scale takes the form of three series of light indicators, the first being graduated in gross steps, the second in increments of a gross step, and the third in fractions of one increment, whereby the readout accurately reflects the prevailing stress level. The tripartite scale is provided with adjustable markers which can be set on the scale to present the stress level at the time a training run is commenced so that subsequent changes in stress level are seen as deviations from the set point.

7 Claims, 1 Drawing Sheet

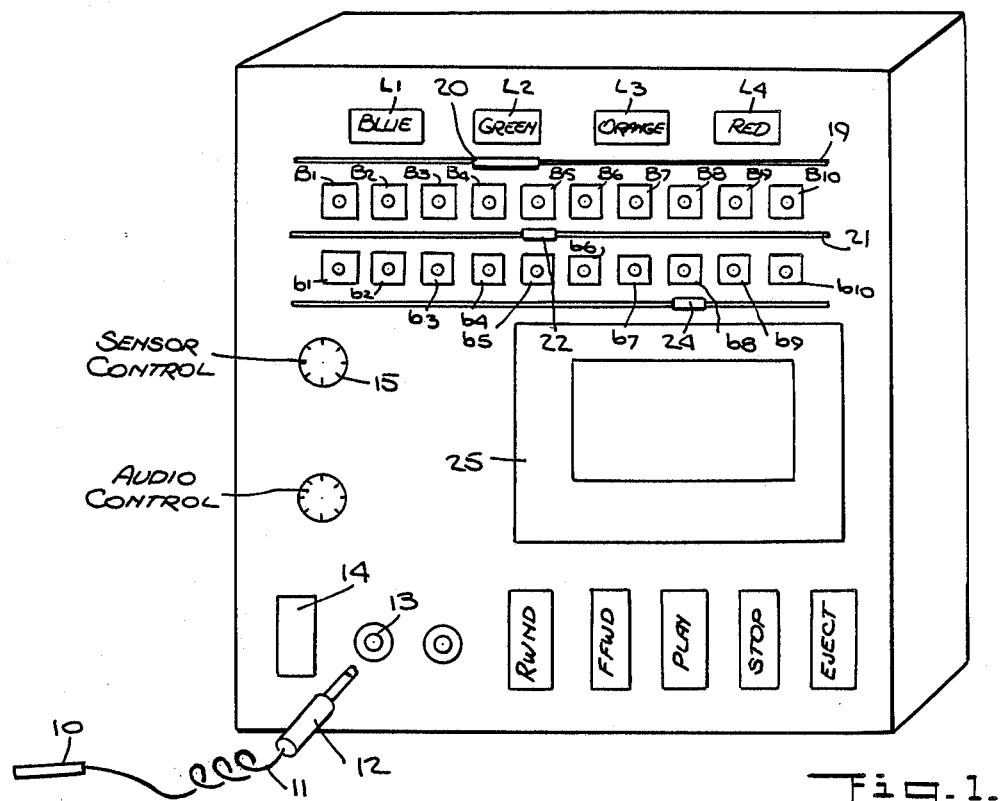
Fig. 1.
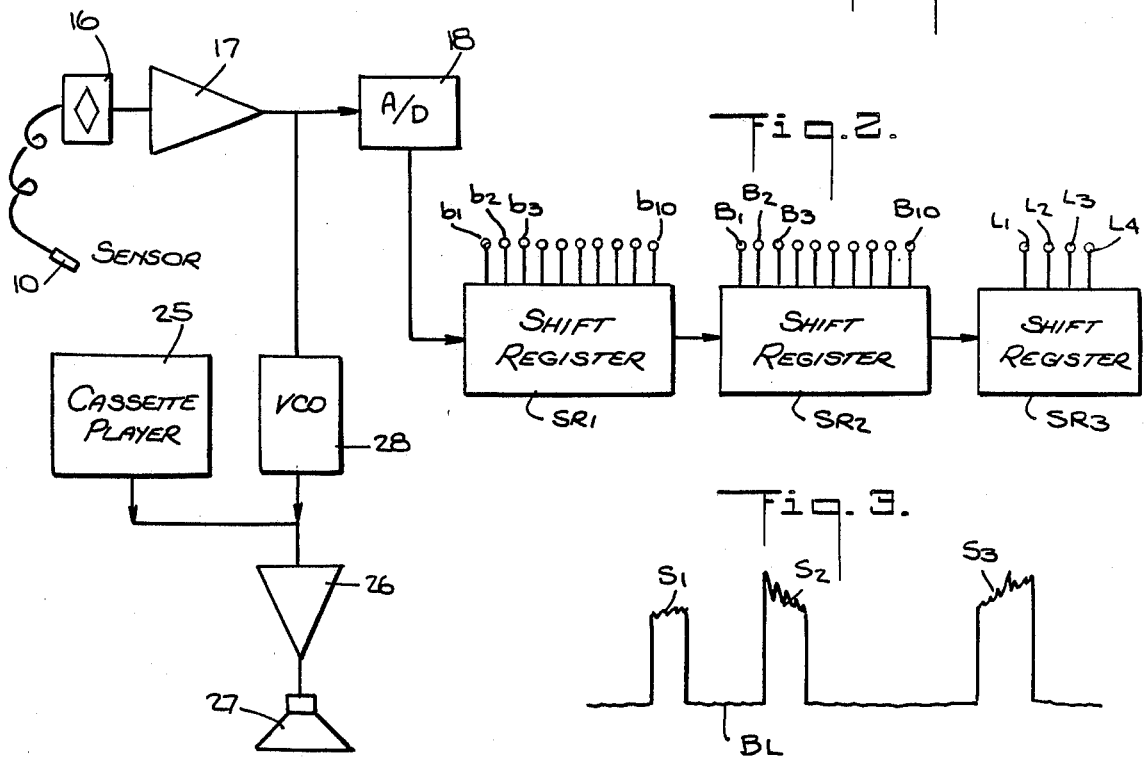
Fig. 2.
Fig. 3.

BIOFEEDBACK THERAPY SYSTEM

BACKGROUND OF INVENTION

1. Field of Invention

This invention relates generally to biofeedback, and more particularly to a biofeedback therapy system in which an individual, while one of his involuntary physiologic functions is being monitored, is intermittently subjected during a training run to stress-inducing stimuli in a manner making it possible for the individual mentally to regulate the function being monitored.

2. Status of the Art

An individual's ability to mentally control certain of his physiological functions such as body temperature or blood pressure is known as self-regulation. For hundreds of years in the Far East, Yogis and Zen Buddhists have practiced the art of self-regulation.

But with the exception of those committed to transcendental meditation, self-regulation techniques have not been widely practiced in Western society, possibly because many disorders induced or aggravated by stress which lend themselves to alleviation by self-regulation can more readily be treated by medication. Thus a muscle contraction or tension headache as well as migraine, a vascular headache that is more painful than a tension headache, can, to some degree, be relieved by aspirin and other drugs. Such medication does not do away with stress factors responsible for the headache but serves only to moderate the symptoms. Moreover, aspirin and other drugs, when taken frequently and in large doses, often have deleterious side effects.

In recent years, biofeedback techniques have been developed which represent a more effective form of self-regulation. In biofeedback, an involuntary or unconscious physiologic process, such as the heart beat or the brain wave, is made perceptible to the senses, thereby making it possible for the individual to manipulate the process by conscious mental control.

Stress is expressed in many ways, and may be manifested by a headache or by high blood pressure. Of overriding importance in stress therapy is learning to relax and thereby reduce tension and its physiological consequences. With biofeedback, one is able to achieve mental and physical relaxation by being fed back information regarding an unconscious physiological process. This information is derived by means of a non-invasive sensor which measures peripheral skin temperature or skin resistance, heart rate, blood pressure, pulse rate, and some other process variables.

Thus a signal from an electromyograph is indicative of varying levels of muscular activity; the higher the signal amplitude, the greater the amount of muscular tension. A high level of muscular tension reflects a high degree of stress, giving rise to tension headaches, facial pain and tics, and other stress-related illnesses. By means of biofeedback, one can monitor a specific physiologic process and derive therefrom a visible or audible signal indicative of the process. In this way, the user can manipulate the process being monitored by learning to control the signal it yields. By biofeedback one can reduce muscle tension, slow down a rapid heart rate, regulate blood flow to alleviate circulatory problems and, in general, relax the nervous system.

The efficacy of biofeedback is well established. Thus, in the article by Sidney Leber, M.D., "Biofeedback in Clinical Psychiatric Practice" appearing in *Psychiatric Opinion* of October 1979, the author states that patients previously dependent on medication for migraine and other stress-related conditions which are responsive to feedback "can reduce their medications to a line of last defense rather than continue to routinely ingest medications as a way of life".

Biofeedback systems which are commercially available come in varying degrees of complexity and sophistication. Thus, Excelsior & Co. of Agoura, Calif., markets a stress control card that measures stress by means of a temperature-sensitive patch that changes color—a red color being indicative of tension, green representing a state of calm, and blue a relaxed state. Printed on the back of the card are mental relaxation techniques.

In order to teach relaxation and stress management techniques, New Frontier, Inc. markets a kit that includes a biofeedback unit manufactured by Farall Instruments, Inc. of Grand Island, Nebr. This unit is provided with an array of color-coded LEDs to provide a visible readout as well as audio feedback. The kit also includes audio relaxation tapes and a training manual.

Thought Technology Ltd., of Montreal, Canada, markets a portable biofeedback system that monitors muscle tension, skin resistance or skin temperature through a headset operating in conjunction with a headband monitor having electrodes therein which engage the forehead.

Lafayette Instrument Company of Lafayette, Ind., offers a biofeedback system which teaches tension control and relaxation, use being made of fingertip electrodes for GSR feedback and a thermistor sensor for temperature feedback. The system also includes an instructional cassette tape.

The difficulty experienced with existing biofeedback systems is that they require a fairly long training period before the user can obtain beneficial effects. The reason for this is that internal stress conditions are not a constant; and when the user first turns on his unit, he may then be in a fairly relaxed state. The unit therefore lacks, as it were, a primer; for unless the user is in a state of stress, he has nothing to work against for purposes of stress management.

Also, existing units do not mark the exact level of stress at the time the unit is first turned on to provide a set point to which the user can refer in determining the extent to which he is able, in the course of a training run, to regulate his stress.

A more serious drawback of existing feedback monitors is that their readout provides only a rough or very general indication of the prevailing state of stress. Thus where the readout is in the form of color-coded indications, such as blue for a relaxed state, yellow for low stress, and red for high stress, this read-out is imprecise. There are various levels of stress, and a red color high-stress indication, for example, does not tell the viewer whether the level of high stress is at the bottom or top of the high stress range or at some intermediate level.

Thus in a training run, the user may succeed in somewhat reducing stress, but to a degree insufficient to cause the color indicator to step from red to yellow. Hence the user will not be informed of his partial success, and this will discourage him from continuing the practice of feedback therapy. Where the feedback is in the form of an audible signal of varying pitch or loudness, this too affords an imprecise indication of stress level.

SUMMARY OF INVENTION

In view of the foregoing, the main object of this invention is to provide a biofeedback therapy system in which the individual, in the course of a training run during which one of his physiologic functions is being continuously monitored, is intermittently subjected to stress-inducing stimuli in a manner making it possible to more effectively regulate the function being monitored.

More particularly, an object of this invention is to provide in a biofeedback system a monitor which visually indicates the physiologic function being sensed along a graduated stress scale, and which includes an adjustable marker that can be set to the scale reading representing the stress level of the individual undergoing training at the time the operation is commenced, this marked reading constituting the set point of the system.

Also an object of the invention is to provide a system in which the stress-inducing stimuli are in audible form and in which the visual reading on the stress scale is accompanied by an audible tone whose pitch corresponds to the scale reading.

Briefly stated, these objects are attained in a biofeedback therapy system in which an individual during a training run in stress control is intermittently subjected to stress-inducing stimuli while one of his physiologic functions is being continuously monitored. The individual is able to observe the effect of the stimuli on a stress-graduated tripartite scale, making it possible for the individual to regulate the function being monitored. The scale takes the form of three series of light indicators, the first being graduated in gross steps, the second in increments of a gross step, and the third in fractions of one increment, whereby the readout accurately reflects the prevailing stress level. The tripartite scale is provided with adjustable markers which can be set on the scale to present the stress level at the time a training run is commenced so that subsequent changes in stress level are seen as deviations from the set point.

OUTLINE OF DRAWINGS

For a better understanding of the invention as well as other objects and further features thereof, reference is made to the following detailed description to be read in conjunction with the accompanying drawings, wherein:

FIG. 1 is a perspective view of one preferred embodiment of a biofeedback unit in accordance with the invention;

FIG. 2 is a block diagram of the electronic components of the unit; and

FIG. 3 shows the wave form of the cassette recording played by the unit.

DESCRIPTION OF INVENTION

Referring now to FIG. 1, there is shown a preferred embodiment of a biofeedback unit in accordance with the invention adapted to monitor a physiologic function whose activity reflects the condition of stress of the individual using the unit.

By way of example, the physiologic function that is sensed by sensor 10 may be skin resistance; for under stress conditions, the skin tends to become moister and hence more conductive electrically. Hence, if sensor 10 consists of spaced electrodes engaging the skin surface, the resistance therebetween will vary as a function of stress. By placing the skin resistance electrodes in a bridge circuit, one can convert skin resistance which is proportional to stress to a corresponding analog voltage.

In the arrangement shown, sensor 10 is coupled by a cable 11 to a plug 12 which is insertable into a socket 13 on the front panel of the unit. Also on this panel is an on-off switch 14 and a sensor output control dial 15.

Sensor 10, as shown in FIG. 2, is coupled to a bridge circuit 16 whose analog voltage output depends on the skin resistance or whatever other physiologic process is being monitored. This analog voltage is applied to an amplifier 17 whose output is fed to an analog-to-digital converter 18. Converter 18 yields pulses whose count is proportional to the analog value derived from the sensor.

The count pulses which reflect the prevailing stress condition are applied to a graduated tripartite scale constituted by three series of light indicators. The third series of indicators is formed by a row of bulbs or other light indicators such as LEDs $b_1$ to $b_{10}$ coupled to the successive stages of a first shift register $SR_1$ to which is applied the incoming pulse count. As a consequence, bulbs $b_1$ and $b_{10}$ are successively actuated when a succession of ten pulses are applied to the register by the converter 18.

The output of shift register $SR_1$ is applied to a second shift register $SR_2$ so that the eleventh pulse acts to reset the first shift register $SR_1$ and to apply a pulse to the second register to cause the first bulb $B_1$ in a second series of indicators $B_1$ to $B_{10}$ to light up.

The output stage of the second shift register $SR_2$ is coupled to the input stage of a third shift register $SR_3$ coupled to a first series of four light indicators $L_1$ to $L_4$, so that after the last bulb $B_{10}$ in the second series is activated and a next pulse is received, this acts to reset the second shift register and to activate the first bulb $L_1$ in the first series.

The four light indicators $L_1$ to $L_4$ in the first series are behind colored glass windows BLUE-GREEN-ORANGE-RED, as shown in FIG. 1, to provide a gross reading of stress. Thus if BLUE is activated, this indicates in gross terms a low level of stress, GREEN being indicative of medium stress, ORANGE of high stress, and RED of very high stress. Below the row of light in the first series is a slot 19 along which is slidable a marker 20 which is settable below any one of the windows.

The reason why the first series provides only a gross reading is that it divides the full spectrum of stress conditions into four discrete steps and does not indicate the stress level within a given step. One does not know from the gross reading whether the stress is at the bottom or top of the step or somewhere in between.

Thus if the full spectrum of stress conditions is covered by an analog voltage from the sensor going from 101 to 140 volts, the BLUE light $L_1$ will go on when the voltage lies in a range of 101 to 110 volts, the GREEN light $L_2$ will go on in the 111 to 120 voltage range, the ORANGE light $L_3$ will go on in the 121 to 130 volt range, and the RED light $L_4$ will go on in the 131 to 140 range. But one looking, say, at the ORANGE light when it is "on" doesn't know from this indication alone whether the stress indicated thereby is at the bottom or top of the high stress range.

The second series of light indicators $B_1$ to $B_{10}$ is behind glass windows which may all have the same color but in progressively deeper shades to provide incremental readings of stress. Thus in the example given, each gross indication provided by indicators $L_1$ to $L_4$ covers a 10-volt step. Hence each of bulbs $B_1$ to $B_{10}$ in the second series represents a one-volt increment so that the full second series is equal to one gross step. Below the row of bulbs $B_1$ to $B_{10}$ is a slot 21 in which a marker 22 is slidable to be set to any one of these bulbs.

The third series of bulbs $b_1$ to $b_2$, which is also behind glass windows on the front panel of the unit, may be in progressively "hot" colors or in progressively deeper shades of the same color to provide a sub-incremental reading. Thus in the example given, each second series increment represents a one-volt advance; hence, each sub-increment in the third series represents one-tenth of a volt. Below the third series of bulbs is a slot in which a marker 24 is slidable.

If, therefore, the analog voltage reflecting the prevailing condition of stress is 105.4 volts and hence within the 101 to 110 volt range, this will activate the low stress (BLUE) gross indicator bulb $L_1$, which is activated anywhere in this range, and it will also activate the increment indicator $B_5$ and the sub-increment indicator $b_4$ to give the exact stress value.

The observer is not concerned with numerical values but only with stress levels in terms of whether they are high or low. Hence the observer does not translate the readout on the graduated scales into numbers, but he is aware that if the BLUE light is on, the stress lies in the low range, and he is advised by the incremental and sub-incremental indicators just how low. If, however, only a gross reading light is on and no other, this tells the observer that the gross reading is at the very bottom of the prevailing low stress condition range. On the other hand, if the sensor output is insufficient to even activate the low stress BLUE gross indicator light, the extent to which the prevailing stress is below this low level will show up on the incremental and sub-incremental indicator scales.

The reason it is important for the user to have a more exact impression of the prevailing stress is that while he might by training be able to somewhat reduce stress rather than to eliminate it, the user's success in this regard will not be manifested should the biofeedback monitor merely provide a gross readout, such as a change in color as one goes from high stress to medium stress.

The user by mental control may have succeeded in somewhat lowering his high stress state, but not to a degree sufficient to produce a medium stress indication, and the user may therefore be led to believe he has failed to accomplish any relaxation in tension. And because of this frustrating sense of failure, the user may be discouraged from persisting in his effort. Yet unless the user persists in biofeedback training, he will not gain any benefit therefrom.

With the present invention, the graduated readout is sensitive to even a minor reduction in stress. This affords positive psychological reinforcement to the user which encourages him to persevere in his efforts to manage stress.

When it is skin temperature that is being measured by means of a thermistor or other temperature sensor having a characteristic thermal lag, because it takes some time for the sensor to yield an output which truly reflects the prevailing temperature, the gradual rise in temperature will first show up in the sub-incremental scale, then the incremental scale, and finally in the gross scale so that the user is aware of this transition and does not receive the impression that the system is not working when it is first turned on.

When sensing peripheral skin temperature, say at a finger, a low temperature is then indicative of high stress; for under stress conditions, the extremities grow cool, not hot, whereas the skin temperature on the face may then rise. Hence where sensed temperature is the yardstick to a stress condition, one must bear in mind how to interpret changes in temperature.

With the present arrangement, the user not only is given a more accurate indication of stress on the tripartite graduated scale, but by means of the adjustable scale markers, he can provide a set point indicative of the stress condition prevailing at the commencement of a training run. In this way the user is able on any given occasion to manipulate the process being sensed in terms of its deviation from the set point and be able therefore to clearly recognize the extent of his success.

To facilitate the training procedure, the system does not depend on the stress condition which the user brings to the instrument, for in some situations the user may begin a training run in a relaxed state and have, as it were, nothing to work against. It is for this reason that the unit is equipped with a magnetic tape cassette player 25 whose output is fed to an amplifier 26 coupled to a loudspeaker 27 or to earphones. Also fed to amplifier 26 is the output of a voltage-controlled oscillator 28. This is responsive to the analog sensor voltage from amplifier 17 to provide an audible tone in loudspeaker 27 whose pitch rises with increasing voltage. Thus, as the stress level goes up, so does the pitch of the tone to heighten the awareness of the observer to the stress condition he is trying to govern.

The tape played back by the cassette player is provided as shown in FIG. 3 with a base level recording BL that induces relaxation, such as so-called white noise or the gentle sound of brook water. This is interrupted intermittently by high-amplitude sounds $S_1$, $S_2$, $S_3$, etc., which induce stress, such as the ring of a telephone, a police siren, a human scream, a loud pistol shot and other startling and disquieting sounds which induce stress.

It is important that these stress-inducing stimuli not occur at predictable times on the cassette recording, but that they should be random, unexpected, and of varying duration. Of course, if the same recording is played repeatedly by the same user of the system, it will lose its impact and not be stress-inducing. Hence a set of different records should be provided which are played in no fixed sequence, so as to retain their effectiveness. Also, one may provide a cassette with relaxation training instructions.

Thus the user in the course of a training run, which is the time it takes to play the tape, is subjected intermittently to stress-inducing sounds, he perceives the effect of each stimulus on the graduated scale as well as by the accompanying feedback tone of varying pitch, and he is therefore able to exercise mental control to relax the resultant stress conditions.

While there has been shown and described a preferred embodiment of BIOFEEDBACK THERAPY SYSTEM in accordance with the invention, it will be appreciated that many changes and modifications may be made therein without, however, departing from the essential spirit thereof. For example, instead of three series of light indicators, one may use graphical gas discharge types of indicators in which an illuminated bar rises and falls along a scale in accordance with the applied analog voltage or pulse count.

I claim:

1. A biofeedback therapy system for training an individual to regulate his internal stress, which individual at the outset of a training run may be in a relatively unstressed state, said system comprising:
   A means including a sensor continuously to monitor a physiologic function of the individual in the course of the training run to produce a signal representing the individual's prevailing level of stress;
   B a scale responsive to said signal to visually indicate the level of stress, making it possible for the individual mentally to regulate the function being monitored; and
   C means to subject the individual being monitored during the course of the training run to a series of startling and disquieting stress-inducing sound stimuli which differ from each other and which appear at random intervals, and are therefore unexpected, to induce internal stress in the individual in the course of the run, said means being constituted by a tape recording having startling sounds recorded thereon at intermittent times which are disturbing to the listener.

2. A system as set forth in claim 1, wherein said sensor measures temperature.

3. A system as set forth in claim 2, wherein said temperature sensor produces an analog voltage which is converted into a digital pulse count that is represented on said scale.

4. A system a set forth in claim 1, wherein said startling sounds are superimposed over a base recording which is relaxation-inducing.

5. A system as set forth in claim 1, wherein said scale is a tripartite scale having a first, a second and third series of sequentially activated light indicators, the first series providing a gross step reading of stress whose general level depends on which indicator in the series is activated; the second series providing a reading in which the step is divided into increments; and the third series providing a reading in which the increment is divided into sub-increments.

6. A system as set forth in claim 5, wherein the three series are displayed in parallel rows on a panel.

7. A system as set forth in claim 6, further including a slidable marker under each row which is settable to a position indicating the stress of the individual at the commencement of the training run, the markers providing a stress set point.

* * * * *